(12) United States Patent
Mizrahi et al.

(10) Patent No.: US 8,876,380 B2
(45) Date of Patent: Nov. 4, 2014

(54) FLUOROSCOPIC DATA DISPLAY

(75) Inventors: Liron Shmuel Mizrahi, Kiryat Haim (IL); Roy Urman, Karkur (IL); Ronen Krupnik, Carmiel (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 213 days.

(21) Appl. No.: 12/978,757

(22) Filed: Dec. 27, 2010

(65) Prior Publication Data

US 2012/0163544 A1 Jun. 28, 2012

(51) Int. Cl.
*A61B 6/10* (2006.01)
*A61B 6/00* (2006.01)
*A61B 5/042* (2006.01)

(52) U.S. Cl.
CPC ............... *A61B 6/107* (2013.01); *A61B 6/462* (2013.01); *A61B 6/467* (2013.01); *A61B 5/0422* (2013.01); *A61B 6/503* (2013.01); *A61B 6/487* (2013.01)
USPC .......................................... 378/203; 378/98.2

(58) Field of Classification Search
USPC ................................. 378/203, 98.2
See application file for complete search history.

(56) References Cited

U.S. PATENT DOCUMENTS

| | | | |
|---|---|---|---|
| 8,338,810 B2* | 12/2012 | Hoernig | 250/515.1 |
| 2004/0202280 A1 | 10/2004 | Besson | |
| 2005/0173658 A1* | 8/2005 | Lemer | 250/515.1 |
| 2005/0256398 A1* | 11/2005 | Hastings et al. | 600/423 |
| 2006/0036125 A1* | 2/2006 | Viswanathan et al. | 600/11 |
| 2006/0284123 A1* | 12/2006 | Goldstein | 250/515.1 |
| 2008/0217564 A1 | 9/2008 | Beyar et al. | |
| 2009/0110152 A1* | 4/2009 | Manzke et al. | 378/195 |

FOREIGN PATENT DOCUMENTS

| | | |
|---|---|---|
| EP | 2 422 702 A1 | 2/2012 |
| JP | 2003-325505 | 11/2003 |
| JP | 2009-178361 | 8/2009 |

OTHER PUBLICATIONS

Extended European Search Report dated Mar. 22, 2012 from related European Application No. 11195137.2.

* cited by examiner

*Primary Examiner* — Hoon Song

(57) ABSTRACT

An apparatus, including a transparent panel, which is configured to protect an operator positioned on a first side of the panel from X-ray radiation applied to a patient on a second side of the panel during a medical procedure, while permitting the operator to view the patient through the panel. The apparatus also includes a display device, which is coupled to present information on the transparent panel responsively to the medical procedure.

10 Claims, 2 Drawing Sheets

FLUOROSCOPIC DATA DISPLAY

FIELD OF THE INVENTION

The present invention relates generally to fluoroscopy, and specifically to a data display used during fluoroscopy.

BACKGROUND

A wide range of medical procedures involve placing objects, such as sensors, tubes, catheters, dispensing devices and implants, within a patient's body. When placing a probe within the body, it may be desirable to track the position of a distal tip of the probe within the body.

The position of the distal tip (or any other portion of the probe within the body, for that matter) can be tracked, for example, by fluoroscopy. Fluoroscopy is an imaging technique which uses X-rays to obtain real-time images of the internal structures of a patient. During fluoroscopy, a patient is positioned between an X-ray generator and an X-ray detector which collects (and sometimes displays) the real-time images. Current fluoroscopy systems typically use a flat panel detector which collects the real-time images and conveys them to a remote console for display.

SUMMARY OF THE INVENTION

There is provided, in accordance with an embodiment of the present invention, an apparatus, including a transparent panel, which is configured to protect an operator positioned on a first side of the panel from X-ray radiation applied to a patient on a second side of the panel during a medical procedure, while permitting the operator to view the patient through the panel, and a display device, which is coupled to present information on the transparent panel responsively to the medical procedure.

In some embodiments, the display device may be positioned on the panel. In another embodiment, the display device may comprise a touchscreen. In an additional embodiment, the apparatus may include a display multiplexer configured to couple the display device to one or more consoles. In an alternative embodiment, the touchscreen may be configured, using the display multiplexer, to present information from the one or more consoles. In a further embodiment, the touchscreen may be configured, using the display multiplexer, to control the one or more consoles. In yet another embodiment, the one or more consoles may be selected from a group consisting of a fluoroscopy unit, a mapping console and an electrocardiography console.

There is further provided, in accordance with an embodiment of the present invention, a method, including protecting, using a transparent panel, an operator positioned on a first side of the panel from X-ray radiation applied to a patient on a second side of the panel during a medical procedure, while permitting the operator to view the patient through the panel, and presenting, using a display device, information on the transparent panel responsively to the medical procedure.

BRIEF DESCRIPTION OF THE DRAWINGS

The disclosure is herein described, by way of example only, with reference to the accompanying drawings, wherein.

DETAILED DESCRIPTION OF EMBODIMENTS

Since fluoroscopy uses X-rays, a form of ionizing radiation, fluoroscopic procedures pose a potential health risk to medical professionals performing the procedures. In an embodiment of the present invention, to reduce exposure to X-ray radiation during a medical procedure such as fluoroscopy, the medical professional (also referred to herein as an operator) typically stands on a first side of a transparent panel. The panel is configured to be opaque to the X-rays, so as to protect the operator from X-radiation applied to a patient on a second side of the panel. A display device, typically positioned on the transparent panel, is coupled to display information on the panel regarding the medical procedure. Examples of displayed information include images of organs involved in the procedure, and diagnostic and control information. The display device may comprise a flat panel display such as a Liquid Crystal Display (LCD) or a Light Emitting Diode (LED) display. Alternatively, the display device may comprise a projection device which projects the images and diagnostic and control information on to the panel.

In some embodiments, the display device may also be touch-sensitive and thus serve as a touchscreen input device. The operator can thus, via the touchscreen, view medical procedure information (e.g., a fluoroscopic image) and interact with any controls (e.g., zooming or selecting a portion of the image) at the same time as viewing the patient through the panel.

In some embodiments, the display may be coupled to, and control one or more consoles in the procedure room. For example, in addition to displaying the fluoroscopic image, the display device may present cardiac mapping information and electrocardiography (ECG) information.

Embodiments of the present invention may help to reduce clutter in the procedure room by eliminating separate video monitors that are normally used to display information from each of the consoles. Combining the panel with a display device, comprising a user interface screen, permits the operator to remain focused on the patient, rather than turning back and forth between the patient and the video monitors and controls.

System Description

Figure 1:
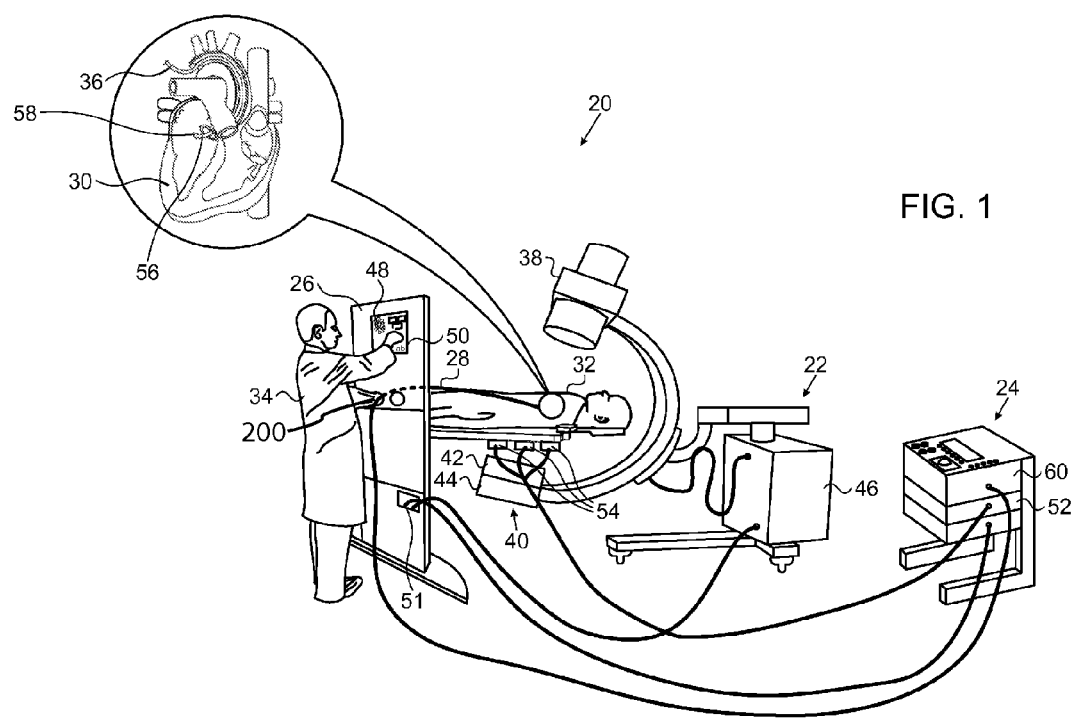
FIG. 1 is a schematic pictorial illustration of a medical procedure room, in accordance with an embodiment of the present invention.
Figure 2:
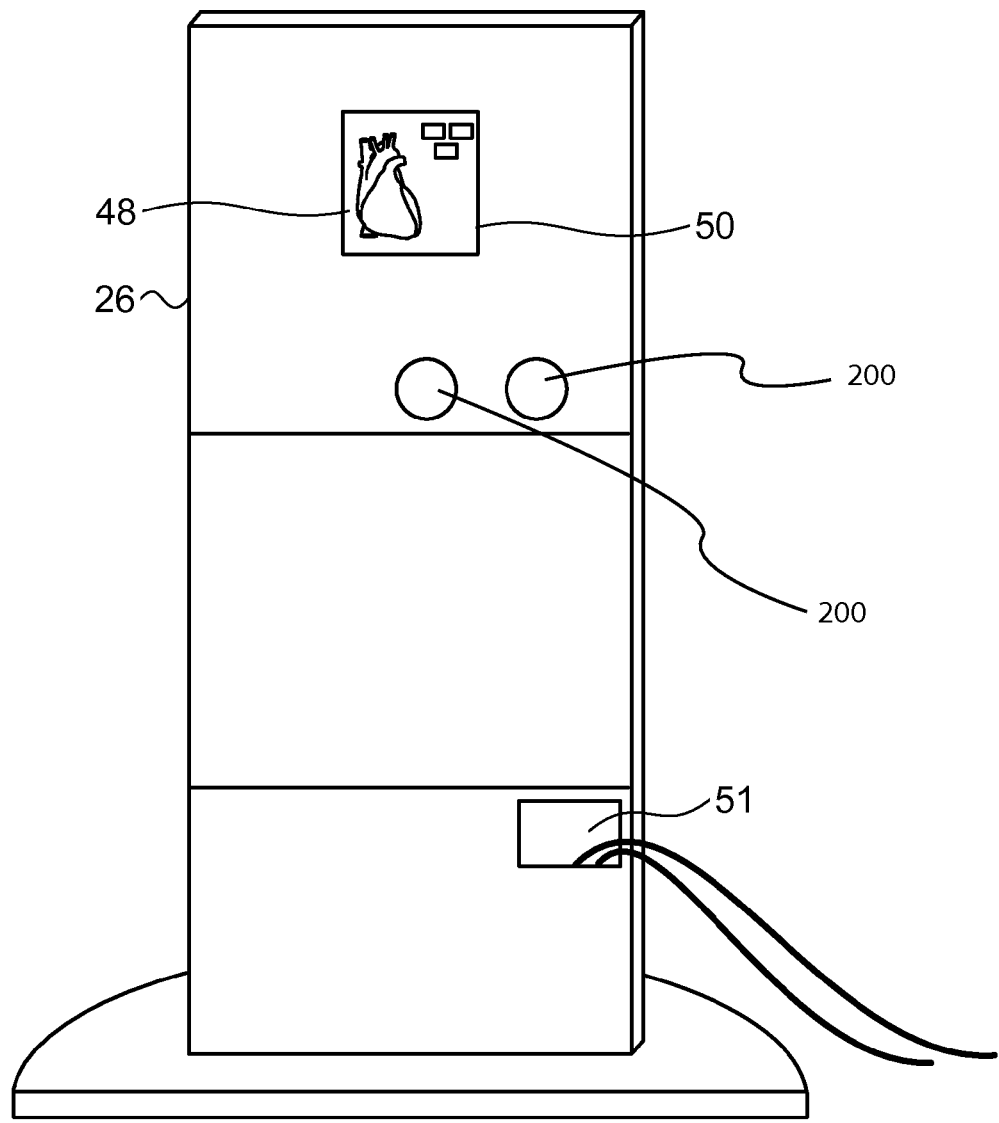
FIG. 2 is a front (perspective) view of an X-ray opaque panel configured with an integrated display device, in accordance with an embodiment of the present invention.

FIG. 1 is an illustration of a medical procedure room 20, and FIG. 2 is a front (perspective) view of a panel 26 in the room, in accordance with an embodiment of the present invention. Room 20 comprises a fluoroscopy unit 22, a mapping console 24, panel 26, and a probe 28. Panel 26 is configured to be transparent to visible radiation but opaque to X-radiation. In the embodiment described hereinbelow, it is assumed that probe 28 is used for diagnostic or therapeutic treatment, such as for mapping electrical potentials in a heart 30 of a patient 32. Alternatively, probe 28 may be used, mutatis mutandis, for other therapeutic (e.g., ablation) and/or diagnostic purposes in the heart or in other body organs.

An operator 34, standing behind panel 26, inserts probe 28 through an opening 200 in the panel 26, and into the vascular system of patient 32 so that a distal end of probe 28 enters a chamber of heart 30. Operator 34 typically uses fluoroscopy to visualize distal end 36 inside heart 30. Fluoroscopy unit 22 comprises an X-ray source 38, positioned above patient 32, which transmits X-rays through the patient. A flat panel detector 40, positioned below patient 32, comprises a scintillator layer 42 which converts the X-rays which pass through patient 32 into light, and a sensor layer 44 which converts the light into electrical signals. Sensor layer typically comprises a two dimensional array of photodiodes, where each photodiode generates an electrical signal in proportion to the light detected by the photodiode.

A fluoroscopy processor 46 converts the electrical signals into an image 48, which the processor presents as information regarding the procedure on a display device 50. Display device is assumed, by way of example, to comprise a flat panel display such as a liquid crystal display (LCD), light emitting diode (LED) display or a plasma display. However other display devices can also be employed to implement embodiments of the present invention. For example display 50 may comprise a cathode ray tube (CRT) display or a projection device which projects image 48 on panel 26. In some embodiments, display device 50 may comprise a touchscreen configured to accept inputs from operator 34, in addition to presenting image 48.

In the configuration shown in FIGS. 1 and 2, display device 50 is positioned on panel 26, which typically comprises an X-ray opaque, visually transparent material configured to both protect operator 34 from X-ray radiation exposure and enable the operator to view patient 32 during the procedure. In embodiments where display device 50 comprises a touchscreen, the touchscreen may be configured to enable operator 34 to control fluoroscopy unit 22 via the touchscreen. Alternatively, an input device such as a keyboard (not shown) may be positioned on panel 26 and configured to control fluoroscopy unit 22.

Additionally, in embodiments where display device 50 comprises a touchscreen, the touchscreen may be configured to control one or more consoles in procedure room 20. For example, in the configuration shown in FIG. 1, display device 50 is coupled, via a display multiplexer 51, to fluoroscopy system 22 and mapping console 24. Operator 34, using the touchscreen, sends commands to, and views information from the consoles, via display multiplexer 51.

Mapping console 24 uses magnetic position sensing to determine position coordinates of distal end 36 inside heart 30. The mapping console comprises a driver circuit 52, which drives field generators 54 placed at known positions external to patient 32, e.g., below the patient's torso. A magnetic field sensor 56 within distal end 36 of probe 28 generates electrical signals in response to the magnetic fields from the coils, thereby enabling console 24 to determine the position of distal end 36 within a chamber of heart 30.

In order to map the cardiac chamber in question, operator 34 positions distal end 36 at multiple positions on (or in close proximity to) the inner surface of the chamber. At each position, an electrode 58 coupled to the distal end measures a certain physiological property (e.g., the local surface electrical potential). Console 24 correlates the position measurements and the electrical potential measurements. Thus, console 24 collects multiple map points, with each map point comprising a coordinate on the inner chamber surface and a respective physiological property measurement at this coordinate.

Console 24 comprises a mapping processor 60, configured to create an intracardiac electrical map based on the collected map points. Mapping processor 60 typically comprises a general-purpose computer, with suitable front end and interface circuits for receiving signals from probe 28 and controlling the other components of console 24. Alternatively, some or all of the functions of processor 60 may be carried out by dedicated or programmable digital hardware components.

In addition to presenting fluoroscopy information, operator 34, may configure display device 50 to present the intracardiac electrical map in image 48. Additionally or alternatively, operator 34 may configure display device 50 to present any diagnostic (i.e., clinical) and control information about the procedure. In other words, operator 34 may configure display device 50 to present information from any console in the procedure room (including, but not limited to fluoroscopy system 22 and mapping console 24). Examples of additional information that can be presented on or controlled by (i.e., in touchscreen embodiments) display device 50 include, but are not limited to:

Adding or removing vital signs such as heart rate, blood pressure, oxygen level, ventilation level.

Adding or removing electrocardiography (ECG) signals, or information derived from the signals, received from an ECG console (not shown). The signals are typically acquired via electrode 58.

During a mapping procedure, alternating between presenting the intracardiac electrical map and presenting the fluoroscopic image.

During a cardiac ablation procedure, showing the location of distal end 36 in heart 30 and/or a force sensing graph showing force applied by the distal end against endocardial tissue.

Manipulating intracardiac maps (e.g., a CARTO™ map). For example, operator 34 can rotate and or zoom in on the map using the touchscreen.

Although FIGS. 1 and 2 show a particular system configuration, other system configurations can also be employed to implement embodiments of the present invention, and are thus considered to be within the spirit and scope of the present invention. Furthermore, the methods described hereinbelow may similarly be applied in therapeutic and diagnostic applications using not only catheters, but also probes of other types, both in the heart and in other body organs and regions.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
a portable transparent panel transparent to visible light and opaque to X-ray radiation, the transparent panel being configured to protect an operator positioned on a first side of the panel from X-ray radiation applied to a patient on a second side of the panel during a medical procedure while permitting the operator to view the patient through the panel, the transparent panel having at least one opening configured to accommodate a medical instrument passing from the first side of the transparent panel to the second side of the transparent panel;

a display device, disposed on the transparent panel, the display device being configured to present information on the transparent panel responsively to the medical procedure; and a display multiplexer configured to couple the display device to a plurality of consoles.

2. The apparatus according to claim 1, wherein the display device comprises a touchscreen.

3. The apparatus according to claim 2, wherein the touchscreen is configured, using the display multiplexer, to present information from the plurality of consoles.

4. The apparatus according to claim 2, wherein the touchscreen is configured, using the display multiplexer, to control the plurality of consoles.

5. The apparatus according to claim 1, wherein the plurality of consoles are selected from a group consisting of a fluoroscopy unit, a mapping console and an electrocardiography console.

6. A method, comprising:

protecting, using a portable transparent panel transparent to visible light and opaque to X-ray radiation, an operator positioned on a first side of the transparent panel from X-ray radiation applied to a patient on a second side of the transparent panel during a medical procedure, while permitting the operator to view the patient through the transparent panel;

passing a medical instrument from the first side of the transparent panel to the second side of the transparent panel through at least one opening formed on a surface of the transparent panel;

presenting, using a display device disposed on the transparent panel, information on the transparent panel responsively to the medical procedure; and coupling the display device to a plurality of consoles via a display multiplexer.

7. The method according to claim 6, wherein the display device comprises a touchscreen.

8. The method according to claim 7, wherein the touchscreen, using the display multiplexer, presents information from the plurality of consoles.

9. The method according to claim 7, wherein the touchscreen, using the display multiplexer, controls the plurality of consoles.

10. The method according to claim 6, wherein the plurality of consoles are selected from a group consisting of a fluoroscopy unit, a mapping console and an electrocardiography console.

* * * * *